(12) United States Patent
Gustin Bergström et al.

(10) Patent No.: US 8,303,565 B2
(45) Date of Patent: Nov. 6, 2012

(54) WAIST BELT FOR AN ABSORBENT ARTICLE WITH VISUAL AIDS

(75) Inventors: Maria Gustin Bergström, Hälsö (SE); Margareta Wennerbäck, Mölnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 475 days.

(21) Appl. No.: 12/430,243

(22) Filed: Apr. 27, 2009

(65) Prior Publication Data
US 2010/0274213 A1 Oct. 28, 2010

(51) Int. Cl.
*A61F 13/15* (2006.01)
(52) U.S. Cl. ............... 604/396; 604/385.01; 604/385.03; 604/386; 604/392
(58) Field of Classification Search ............. 604/385.01, 604/385.03, 386, 396, 392
See application file for complete search history.

(56) References Cited

U.S. PATENT DOCUMENTS

| | | | |
|---|---|---|---|
| 6,342,050 | B1 | 1/2002 | Rönnberg et al. |
| 2002/0032425 | A1 | 3/2002 | Hjorth |
| 2003/0158532 | A1 | 8/2003 | Magee et al. |
| 2006/0021536 | A1 | 2/2006 | Song et al. |
| 2007/0032773 | A1 | 2/2007 | Magee et al. |
| 2008/0097369 | A1 | 4/2008 | Melander |

FOREIGN PATENT DOCUMENTS

| | | |
|---|---|---|
| JP | 2004-261354 | 9/2004 |
| WO | 02/49568 | 6/2002 |
| WO | 2005/023160 | 3/2005 |
| WO | 2008/001330 | 1/2008 |

OTHER PUBLICATIONS

U.S. Appl. No. 12/186,890, filed Aug. 6, 2008, Bogdanova.

*Primary Examiner* — Jacqueline F. Stephens
(74) *Attorney, Agent, or Firm* — Drinker Biddle & Reath LLP

(57) ABSTRACT

An absorbent article includes an absorbent section having first and second end portions and a central portion. A waist belt is attached to the absorbent section at its first end and has first and second belt portions extending on each side of the first end of the absorbent section for securing to each other around a wearer of the absorbent article. The second end of the absorbent section includes a fastening device for securing the second end of the absorbent section to the waist belt. The waist belt has a visual appearance different from the absorbent section, so as to simulate a belt. This provides the user with intuitive information on how the absorbent article should be applied.

38 Claims, 3 Drawing Sheets

WAIST BELT FOR AN ABSORBENT ARTICLE WITH VISUAL AIDS

FIELD OF THE INVENTION

The present invention relates to a waist belt for an absorbent article. More particularly, the present invention relates to a waist belt for an absorbent article with visual aids for easier application.

BACKGROUND OF THE INVENTION

Absorbent articles in the form of disposable diapers are generally known in which the diaper is provided with a fastening system including a pair of fastening tabs secured to both sides of one end region of the diaper. The fastening tabs are intended to engage receiving means located on the other end region of the diaper. Such a diaper is generally placed on the wearer when the wearer is lying down. While the above-described fastening arrangement is satisfactory when applying diapers to a young child or baby, problems can arise when trying to fit an incontinence diaper to an adult wearer. This is particularly true for wearers who wish to apply the diaper to themselves, or for caregivers who receive a significant benefit from applying the diaper when the wearer is in a standing position.

To address this issue, a belted absorbent article has been developed, which allows a wearer or caregiver to apply the diaper in a standing position. An example of such a belted absorbent article is described in U.S. Pat. No. 6,342,050, which is incorporated herein by reference. Typically, the absorbent article has a belt attached integrally with the absorbent article. The belt may have two belt portions extending on either side of the rear end of the absorbent section. The two belt portions are intended to be fastened around the waist of the wearer while the front end of the absorbent section hangs down between the legs of the wearer. Once the belt portions have been joined together, the wearer can reach between his or her legs to draw up the absorbent section between the legs and to attach the free end of the absorbent section to the belt portion.

Similarly, the article can be made so that the belt is fastened to the front portion of the product and is secured around the back of the wearer. In this case, the absorption section will be hanging down in the front and will be secured to the belt in the back. This type of product is particularly useful for caregivers who care for patients that may have dementia or the like. It should be noted that this type of configuration is not ideal for wearers who wish to apply the article themselves.

Where the problem of incontinence is involved, it will be appreciated that persons suffering from this problem are often old and have physical handicaps of various types. As a consequence, they may have more difficulty fastening the belt by themselves and often require the assistance of personnel for fitting the articles. However, it has been discovered that both caregivers and users have difficulty understanding how the product should be applied. With regard to belted articles, an important aspect is that the caregiver or user understand that the long extending portions are attached around the waist like a belt. Although directions of application may be included with the article packaging, the instructions are often ignored or thrown away. Therefore, the user becomes frustrated with the product.

Accordingly, there is a need in the art to provide a waist belt product that can be more intuitively applied to the user.

SUMMARY

According to a first aspect of the invention, an absorbent article comprises an absorbent section, the absorbent section having first and second end portions and a central portion therebetween, a waist belt attached to the absorbent section, the waist belt having first and second belt portions extending on each side of the first end portion of the absorbent section for securing to each other around a wearer of the absorbent article, the second end portion of the absorbent section including a fastening device for securing the second end portion of the absorbent section to the waist belt, wherein a garment facing side of the first and second belt portions of the waist belt has a visual appearance different from the central portion of the absorbent section and the garment facing side of the first end portion of the absorbent section includes a visual cue portion.

According to a second aspect of the invention, an absorbent article comprises an absorbent section, the absorbent section having first and second end portions and a central portion therebetween, a waist belt attached to the absorbent section, the waist belt having first and second belt portions extending on each side of the first end portion of the absorbent section for securing to each other around a wearer of the absorbent article, the second end portion of the absorbent section including a fastening device for securing the second end portion of the absorbent section to the waist belt, wherein a garment facing side of the first and second belt portions of the waist belt has a visual appearance different from the central portion of the absorbent section and a garment facing side of the second end portion of the absorbent section includes a visual cue portion.

According to a third aspect of the invention, an absorbent article comprises an absorbent section, the absorbent section having first and second end portions and a central portion therebetween, a waist belt attached to the absorbent section, the waist belt having first and second belt portions extending on each side of the first end portion of the absorbent section for securing to each other around a wearer of the absorbent article, the second end portion of the absorbent section including a fastening device for securing the second end portion of the absorbent section to the waist belt, wherein a garment facing side of the first and second belt portions of the waist belt has a visual appearance different from the central portion of the absorbent section and garment facing sides of the first and second end portions of the absorbent section include a visual cue portion.

Yet a further feature of the present invention is that the garment facing side of the first and second belt portions of the waist belt and the visual cue portion of the garment facing side of the first end portion of the absorbent section are colored, patterned, or textured to give the appearance of a continuous belt. In addition, the visual cue portion of the garment facing side of the second end portion of the absorbent section may have the same color, pattern, or texture as the visual cue portion of the garment facing side of the first end portion of the absorbent section. These further features apply to each of the three aspects described above.

Still yet a further feature of the present invention is that a first end of one of the first and second belt portions of the waist belt includes a grip portion. The grip portion may be provided in a different color, texture or shape from adjacent areas on the garment facing side of the first and second belt portions of the waist belt. These further features apply to each of the three aspects described above.

Yet another feature of the present invention is that a garment facing side of the second end portion of the absorbent section includes a visual cue portion that is provided has a different appearance than the central portion of the absorbent section. The visual cue portion of the garment facing side of the second end portion of the absorbent section may be the grip portions, which are disposed on ends of the second end portion, and/or a colored, patterned or textured section extending across the second end portion. The grip portions may have a different color, pattern, texture or shape than adjacent areas on the garment facing side of the second end portion of the absorbent section. These further features apply to each of the three aspects described above.

Still further, another feature of the present invention is that the user facing side of the first and second belt portions of the waist belt and a user facing side of the first end portion of the absorbent section have a visual appearance different from the central portion of the absorbent section. In addition, the garment facing side of the waist belt and the user facing side of the waist belt may be provided in the same color, pattern, or texture or a different color, pattern, or texture. The fastening device for securing the second end portion of the absorbent section to the waist belt may have the same appearance as the garment facing side of the first and second belt portions. Additionally, visual instructions may be included on the absorbent article wherein an article pictured in the visual instructions has the same appearance as the actual absorbent article. These further features apply to each of the three aspects described above.

Each of the features described above may be taken alone or in any possible combination for an enhanced effect of directing a user on how to apply the article.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements.

DETAILED DESCRIPTION OF THE PREFERRED EMBODIMENTS

Figure 1:
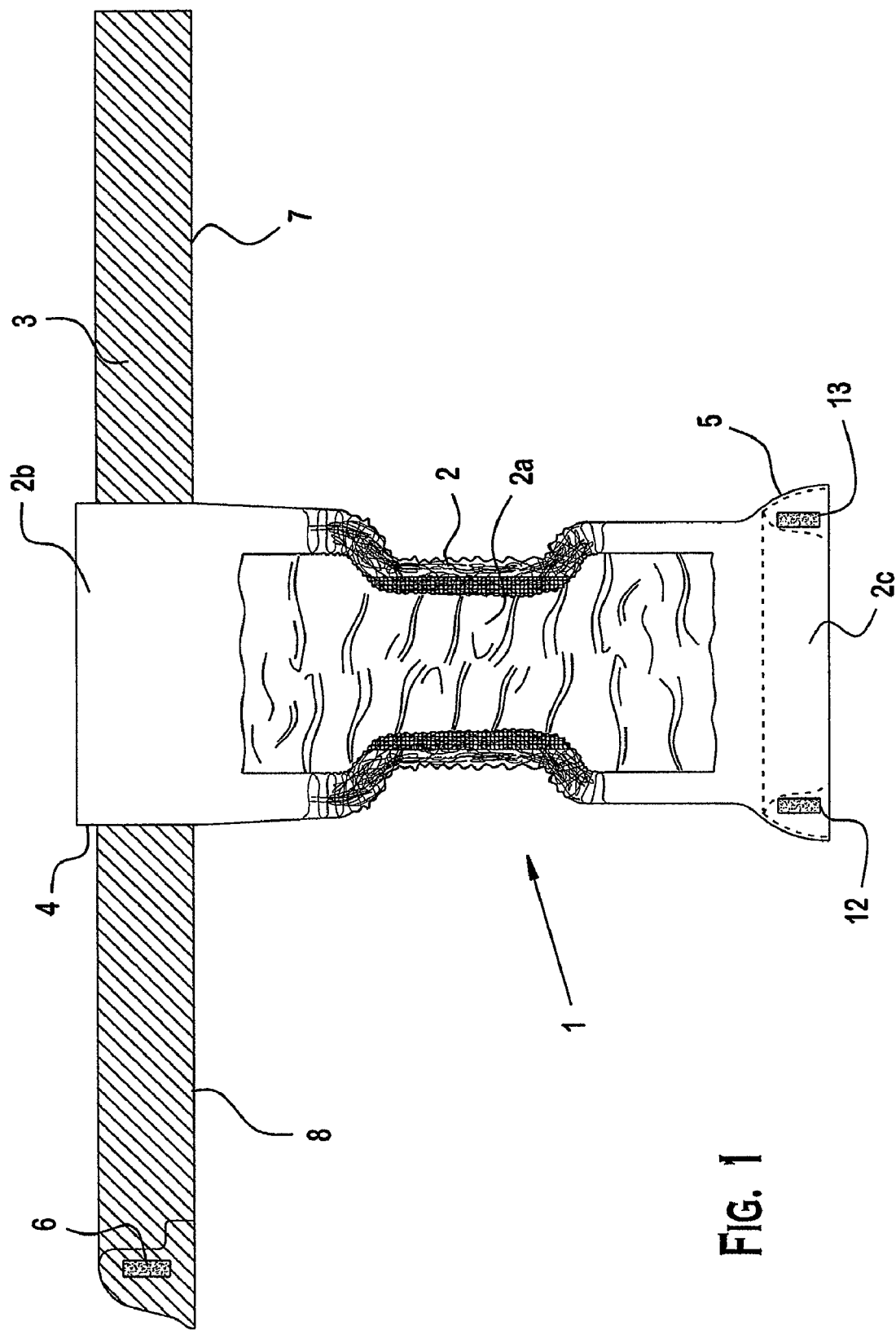
FIG. 1 is a top plan view of a user facing side of a belted absorbent article according to the present invention.
Figure 5:
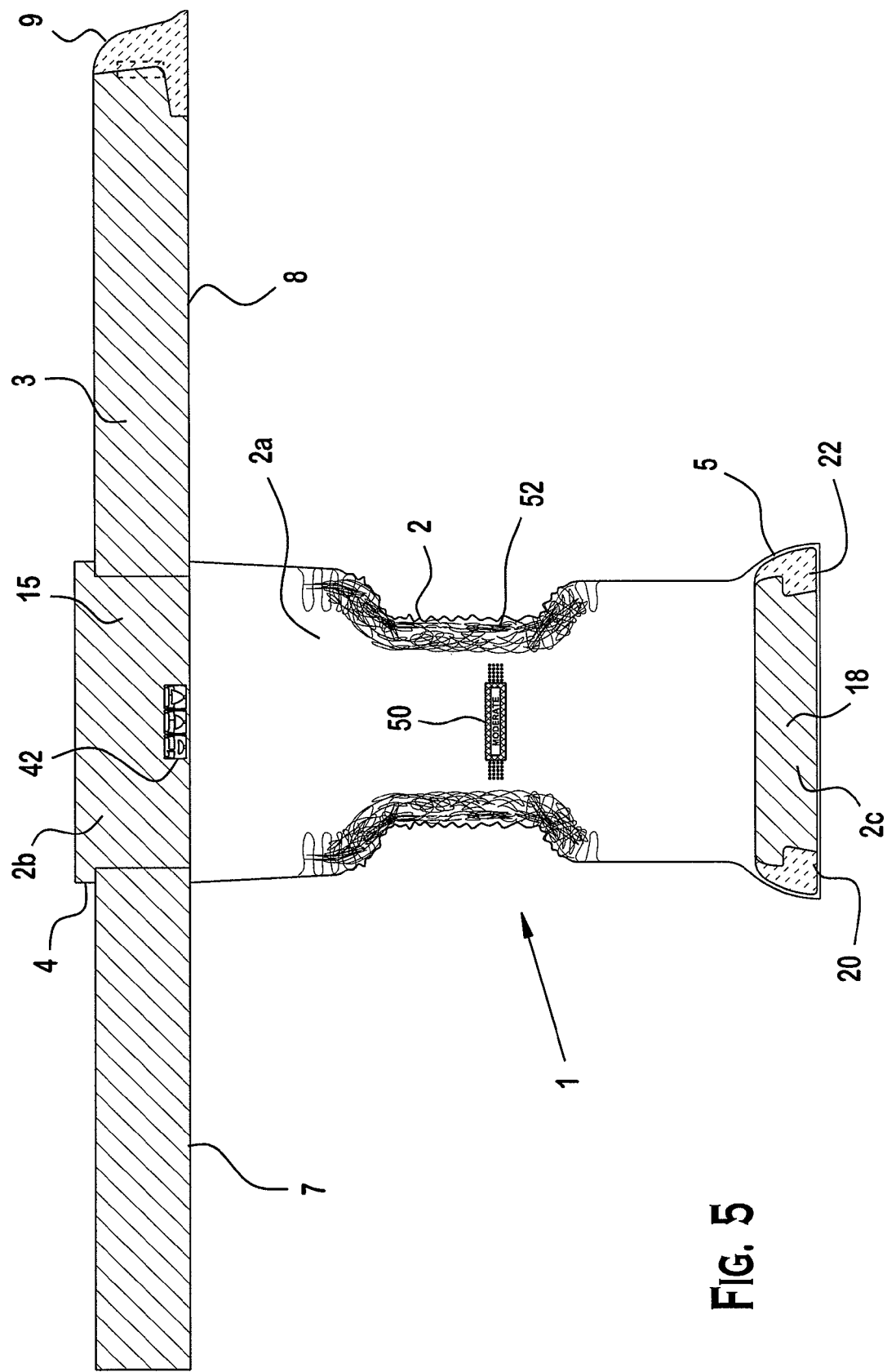
FIG. 5 is a top plan view of a garment facing side of the belted absorbent article according to the present invention.

FIGS. 1 and 5 show an absorbent article generally denoted 1 which includes an absorbent section 2, a belt portion generally denoted 3, and a first end 4 and a second end 5. The first end 4 may be either at a rear or front of the absorbent article 1. The absorbent section 2 includes a central portion 2a and first and second end portions 2b and 2c, respectively. The belt 3 could be either one continuous belt 3 attached to one of the first or second end portions 2b or 2c, or could be two separate belt portions 7 and 8 each attached to respective sides of either the first end portion 2b or second end portion 2c. The present invention pertains to providing further visual cues to aid a user or caregiver to determine how the belted absorbent article should be applied.

With reference to FIG. 1, the user facing side of the absorbent article 1 includes a fastening device 6 disposed at an end of the belt portion 3. Preferably, the fastening device 6 is a strip of hook elements which can either be secured to the belt portion 7 or to a loop strip arranged on the belt portion 7. However, it should be understood that other types of fastening devices are possible, including but not limited to, adhesive, pressure buttons, buttons and button holes, knots, and strings. The fastening device 6 may include visually distinguishing features, such as a different color or pattern than adjacent areas on the user facing side or interior of the belt 3.

Disposed on the second end portion 2c of the absorbent section 2 of the article 1 are fastening devices 12 and 13. Preferably, fastening devices 12 and 13 are flexible strips of hook elements, which can be secured directly to the belt 3. However, it should be understood that other types of fastening devices are possible, including but not limited to, adhesive, pressure buttons, buttons and button holes, knots, and strings. The fastening devices 12 and 13 may also include visually distinguishing features, such as a different color or pattern than adjacent areas on the user facing side of the second end portion 2c.

Alternatively, the fastening devices 12 and 13 may be one continuous colored band arranged across the user side of the second end portion 2c (not shown). The continuous colored band preferably has the same color and/or pattern as the garment facing side of the belt 3. Likewise, the fastening devices 6, 12, and 13 may also have the same color and/or pattern as the garment facing side of the belt 3. In this way, the user is directed to match the internal fastening devices to the garment facing side or exterior of the belt 3.

Figure 2:
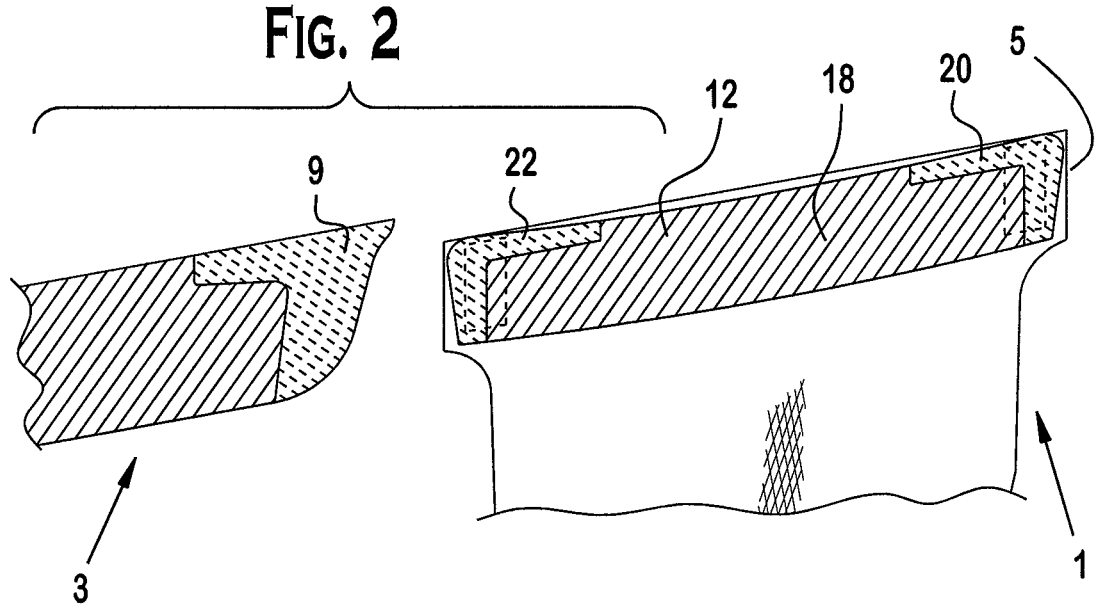
FIG. 2 is a partial view of the garment facing side of the front portion of the absorbent article and a partial view of a garment facing side of an end portion of the belt portion according to the present invention.

To further aid in securing the belt, one of the belt portions 7 or 8 may include a grip portion. With reference to FIGS. 2 and 5, the end of the belt portion 8 preferably includes a grip portion 9, although it should be understood that belt portion 7 may also have a grip portion. The grip portion 9 directs the user to grip the belt portion 8 for attachment thereof to the other belt portion 7. As such, the grip portion 9 is an area that is visually and/or texturally distinct from areas nearby. Preferably, the grip portion 9 has a different shape, texture or color so as to intuitively direct a user to grip the belt portion 8 at the grip location. Accordingly, the user or caregiver will be directed to grip the belt portion 8 at the grip location when fastening the belt around the waist of a user. The grip portion 9 is located near the edge of the belt 3 at/near the location of the hook strip, but on the opposite side. That is, the grip portion 9 is preferably located on the garment facing side, while on the opposite side of the belt portion 8, the fastening device 6 is located on the user side. Alternatively, the grip portion 9 may be provided on both the user facing side of the belt portion 8, as shown for example, in FIG. 1, and the garment facing side of the belt portion 8, as shown for example, in FIG. 5.

With reference to FIG. 5, the garment facing side of the belt 3 (i.e., belt portions 7 and 8) preferably has an appearance that distinguishes the belt 3 from the central portion 2a of the absorbent section 2. That is, the garment facing side of the belt 3 may be colored, patterned, and/or textured in a different color, pattern, and/or texture than the central portion 2a of the absorbent section 2. In addition, a visual cue portion 15 may be provided at the first end portion 2b of the absorbent section 2 of the article 1. The visual cue portion 15 is defined as an area having a visual appearance different from the central portion 2a of the absorbent section 2. For example, the visual cue portion 15 may include a color, pattern and/or texture that distinguishes the portion 15 from the central portion 2a. A width of the visual cue portion 15 is preferably at least the same width as the belt portions 7 and 8, but may be slightly larger or smaller, depending on design preference. As such, the portions 7, 8 and 15 give an appearance of an actual, continuous belt, and are set apart from the central portion 2a of the absorbent section 2, providing a visual cue that the portions 7 and 8 are formed as a belt and should be fastened as a belt together.

However, it should be understood that the portions 7, 8 and 15 may include other patterns, colors, and/or textures, so long as the portions 7, 8 and 15 give the appearance of being a continuous belt. That is, the portions 7, 8 and 15 may not be identical in appearance, but may still give a visual cue that the portions 7, 8 and 15 are a continuous belt. In addition, the entire garment facing sides of belt portions 7 and 8 need not be visually different, only the parts that would be visible upon application of the belt 3 around the waist of the user. For example, the end portion of belt portion 7 need not be visually different because upon application of the belt 3 around the waist of the user, the end portion of the belt portion 7 is hidden from view. In addition, different colors, patterns, and/or textures may be used to indicate different sizes and/or absorbency levels.

With continued reference to FIGS. 2 and 5, the second end portion 2c of the absorbent section 2 of the garment facing side of the absorbent article 1 may include a visual cue portion. The visual cue portion is defined as an area having a visual appearance different from the central portion 2a of the absorbent section 2. For example, the visual cue portion may be a colored, patterned or textured section 18 that extends across the front of the second end portion 2c. In this regard, the section 18 may have the same color/pattern/texture as the visual cue portion 15. This provides the attached article 1 with a body surrounding colored belt area. However, it should be understood that a colored, patterned and/or textured section 18 need not be provided.

Preferably, the belt portions 7 and 8 are made from a pre-colored nonwoven fabric. Alternatively, the belt portions 7 and 8 may be white, with the appropriate color, pattern, and/or texture printed or imprinted on the fabric. Likewise, the visual cue portions 15 and 18 are preferably generated by printing and/or applying a color or pattern to an absorbent article 1, or in the case of a texture, imprinting the texture. Typically, the absorbent article 1 will be white, and the color, pattern, and/or texture will be printed or imprinted on the white absorbent article 1. Alternatively, the visual cue portions 15 and 18 may applied during the manufacturing process of the absorbent article 1.

With continued reference to FIGS. 2 and 5, grip portions 20 and 22 may be provided on the garment facing side of the second end portion 2c. The grip portions 20 and 22 direct the user to grip the second end portion 2c of the article 1 for attachment thereof to the fastened belt 3. As such, the grip portions 20 and 22 are areas that are visually and/or texturally distinct from areas nearby. Preferably, the grip portions 20 and 22 have a different shape, texture or color so as to intuitively direct a user to grip the second end portion 2c of the absorbent section 2 at the grip location. Accordingly, the user or caregiver will be directed to grip the second end portion 2c when fastening the absorbent section 2 to the belt 3, which is already fastened around the waist of a user. In addition, the grip portions 20 and 22 may be visually or texturally different from the section 18 and may act as further visual cue portions of the section 18. For example, the section 18 may be non-colored or white, while the grip portions 20 and 22 act as the visual cue portion.

The grip portions 20 and 22 are preferably located on side ends of the second end portion 2c at/near the location of the fastening devices 12 and 13, but on the opposite side. That is, the grip portions 20 and 22 are preferably located on the garment facing side of the second end portion 2c, while on the user facing side of the second end portion 2c, the fastening devices 12 and 13 are located directly opposite. Alternatively, the grip portions 20 and 22 may be provided on both the garment facing side of the second end portion 2c and user facing side of the second end portion 2c. In addition, the grip portions 20 and 22 and the grip portion 9 on the belt 3 may have the same color, pattern or texture to give an overall impression of where the article 1 should be gripped for application.

In use, the two belt portions 7 and 8 are intended to be fastened around the waist of the wearer while the second end portion 2c of the absorbent section 2 hangs down between the legs of the wearer. Once the belt portions 7 and 8 have been joined together, the wearer can reach between his or her legs to grab absorbent section 2 by its grip portions 20 and 22, draw it up between his or her legs, and attach the second end portion 2c of the absorbent section 2 to the belt 3. In addition, the colored fastening devices 12 and 13 which preferably match the exterior color and/or appearance of the belt 3, provide yet another visual cue that the second end portion 2c of the absorbent section 2 should be attached to the belt 3.

With reference back to FIG. 1, the user facing side of the absorbent article 1 will be further described. Like the garment facing side of the absorbent article 1, the belt portions 7 and 8 of the user facing side may be visually different. However, it should be understood that the user facing side of portions 7 and 8 may include other patterns, colors, and/or textures.

To further distinguish the belt, the garment facing side of belt portions 7 and 8 of the belt 3, as shown in FIG. 5, may be made from a different color, pattern, and/or texture than the user facing side of the belt portions 7 and 8, shown in FIG. 1. This might provide yet another visual cue as to how the belt 3 should be secured around the waist of the user. Alternatively, both the garment facing sides and user facing sides of the belt portions 7 and 8 could be provided in the same color, pattern and/or texture, or varying colors, patterns and/or textures.

Instead of using different colors, other types of differentiating patterns or textures may be used, so long as the belt 3 and/or visual cue portions 15 and 18 look visually different than the central portion 2a of the absorbent section 2 of the article 1. For example, the belt 3 and/or visual cue portions 15 and 18 may be patterned, while the central portion 2a of the absorbent section 2 is not, or vice versa. In addition, the belt 3 and/or visual cue portions 15 and 18 may be shaded in a different color than the central portion 2a of the absorbent section 2.

Figure 3:
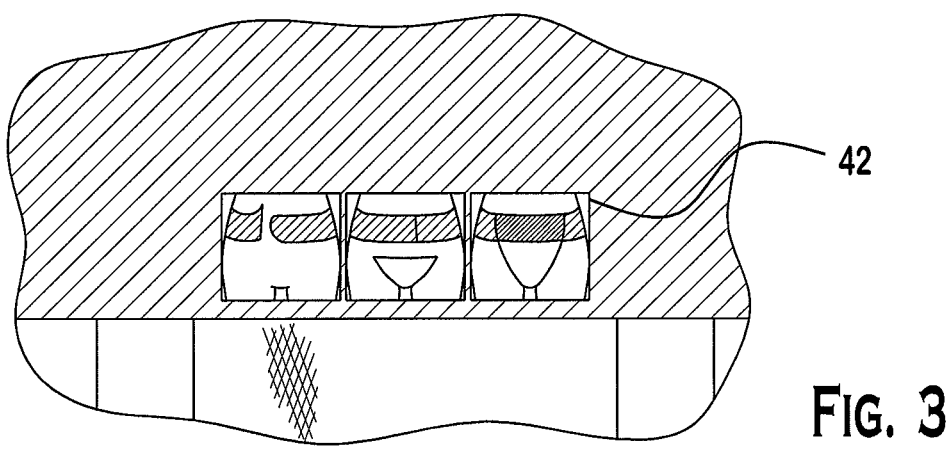
FIG. 3 is a partial view of the garment facing side of the back portion of the belted absorbent article displaying visual instructions according to the present invention.

With reference to FIGS. 3 and 5, visual instructions 42 for using the article may be provided on a portion of the absorbent section 2 or belt 3. Preferably, the visual instructions 42 are a series of pictorial diagrams showing the basic steps for applying the article. Other types of instructions are possible, such as written instructions alone or written instructions together with pictorial instructions. In addition, the instructions may change depending on the particular structure and application of the article. Accordingly, the present invention is not limited to the pictorial instructions described in the preferred embodiment. In addition, the instructions may be more or less detailed, or related to disposal of the article.

The instructions may be placed on the article 1 in various places. Preferably, the instructions 42 are placed on a garment facing side on the first end portion 2b of the absorbent section 2, as shown in FIG. 5. However, it should be understood that instructions may be placed at any location on the article, so long as it is relatively visible to the wearer or caregiver.

The instructions 42 may also be placed on the inside of the waist edge along the second end portion 2c of the absorbent section 2. In this embodiment, the instructions 42 are visible to the user once the article 1 is disposed between the legs of the user. The instructions 42 may also be placed on the article strategically so that during the course of applying the article, the instructions become visible at that particular point in the process. For example, the instructions 42 may be applied at one of the grip portions 9, 20, and/or 22. As shown in FIG. 3, the pictorial instructions 42 may be colored, patterned, or textured precisely as the actual article. That is, the belt and other portions that are colored, patterned, and/or textured may be presented similarly in the visual instructions 42 to even more clearly illustrate how to use the article. A more detailed discussion of the pictorial instructions may be found in U.S. patent application Ser. No. 12/186,890, which is incorporated by reference herein.

Figure 4:
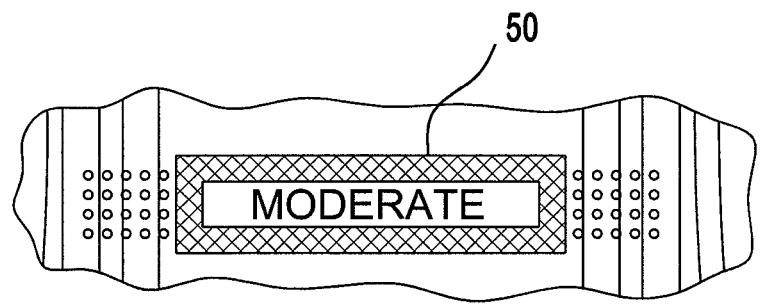
FIG. 4 is a partial view of the crotch portion of the garment facing side of the belted absorbent article providing information on the absorbency level of the article according to the present invention.

With reference to FIGS. 4 and 5, an absorbency indicator 50 of the article 1 may be included at a folding that is preferably in the middle of the absorbent section 2 along the crotch portion 52. Preferably, the absorbency indicator 50 is disposed at such a location and size such that when the article is in a folded position, the absorbency level 50 may be easily read from the article. That is, when the article is lying on a shelf in, for example, a nursing home, the indicator 50 is clearly visible.

It should be noted that, while the term "absorbent article" has been used particularly in conjunction with incontinence, and particularly adult incontinence, the invention is not limited to this particular use or any particular size or type of absorbent article implied thereby. The above-described article and method could be used with baby's or children's diapers.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

The invention claimed is:

1. An absorbent article, comprising:
    an absorbent section, the absorbent section having first and second end portions and a central portion therebetween;
    a waist belt attached to the absorbent section, the waist belt having first and second belt portions extending on each side of the first end portion of the absorbent section such that the first and second belt portions can be secured directly to each other around a wearer of the absorbent article, at least one of the belt portions including a fastening device for securing the two belt portions directly to each other around a wearer of the absorbent article, the second end portion of the absorbent section including a fastening device for securing the second end portion of the absorbent section to the waist belt;
    wherein a garment facing side of the first and second belt portions of the waist belt has a visual appearance different from the central portion of the absorbent section and the garment facing side of the first end portion of the absorbent section includes a visual cue portion.

2. The absorbent article of claim 1, wherein the garment facing side of the first and second belt portions of the waist belt and the visual cue portion of the garment facing side of the first end portion of the absorbent section are colored, patterned, or textured to give the appearance of a continuous belt.

3. The absorbent article of claim 1, wherein a first end of one of the first and second belt portions of the waist belt includes a grip portion.

4. The absorbent article of claim 3, wherein the grip portion is provided in a different color, pattern, texture or shape than a color, pattern, texture or shape of adjacent areas on the garment facing side of the first and second belt portions of the waist belt.

5. The absorbent article of claim 1, wherein a garment facing side of the second end portion of the absorbent section includes a visual cue portion that has a different appearance than the central portion of the absorbent section.

6. The absorbent article of claim 5, wherein the visual cue portion of the garment facing side of the second end portion of the absorbent section includes grip portions disposed on ends of the second end portion, the grip portions having a different color, pattern, texture or shape than adjacent areas on the garment facing side of the second end portion of the absorbent section.

7. The absorbent article of claim 5, wherein the visual cue portion of the garment facing side of the second end portion includes a colored, patterned or textured section extending across the second end portion.

8. The absorbent article of claim 5, wherein the visual cue portion of the garment facing side of the second end portion of the absorbent section has the same color, pattern, or texture as the visual cue portion of the garment facing side of the first end portion of the absorbent section.

9. The absorbent article of claim 1, further including visual instructions disposed on the absorbent article, wherein an article pictured in the visual instructions has the same appearance as the actual absorbent article.

10. The absorbent article of claim 1, wherein a user facing side of the first and second belt portions of the waist belt and a user facing side of the first end portion of the absorbent section have a visual appearance different from the central portion of the absorbent section.

11. The absorbent article of claim 1, wherein the garment facing side of the waist belt and the user facing side of the waist belt are provided in the same color, pattern, or texture.

12. The absorbent article of claim 1, wherein the garment facing side of the waist belt and the user facing side of the waist belt are provided in a different color, pattern, or texture.

13. The absorbent article of claim 1, wherein the fastening device for securing the second end portion of the absorbent section to the waist belt has the same appearance as the garment facing side of the first and second belt portions.

14. An absorbent article, comprising:
    an absorbent section, the absorbent section having first and second end portions and a central portion therebetween;
    a waist belt attached to the absorbent section, the waist belt having first and second belt portions extending on each side of the first end portion of the absorbent section such that the first and second belt portions can be secured directly to each other around a wearer of the absorbent article, at least one of the belt portions including a fastening device for securing the two belt portions directly to each other around a wearer of the absorbent article, the second end portion of the absorbent section including a fastening device for securing the second end portion of the absorbent section to the waist belt;
    wherein a garment facing side of the first and second belt portions of the waist belt has a visual appearance different from the central portion of the absorbent section and a garment facing side of the second end portion of the absorbent section includes a visual cue portion.

15. The absorbent article of claim 14, wherein the garment facing side of the first end portion of the absorbent section includes a visual cue portion.

16. The absorbent article of claim 15, wherein the garment facing side of the first and second belt portions of the waist belt and the visual cue portion of the garment facing side of the first end portion of the absorbent section are colored, patterned or textured to give the appearance of a continuous belt.

17. The absorbent article of claim 14, wherein a first end of one of the first and second belt portions of the waist belt includes a grip portion.

18. The absorbent article of claim 17, wherein the grip portion is provided in a different color, pattern, texture or shape than a color, pattern, texture or shape of adjacent areas on the garment facing side of the first and second belt portions of the waist belt.

19. The absorbent article of claim 15, wherein the visual cue portion of the garment facing side of the second end portion of the absorbent section has the same color, pattern, or texture as the visual cue portion of the garment facing side of the first end portion of the absorbent section.

20. The absorbent article of claim 14, wherein the visual cue portion of the garment facing side of the second end portion of the absorbent section include grip portions disposed on ends of the second end portion, the grip portions having a different color, pattern, texture or shape than adjacent areas on the garment facing side of the second end portion of the absorbent section.

21. The absorbent article of claim 14, wherein the visual cue portion of the garment facing side of the second end portion includes a colored, patterned, or textured section extending across the second end portion.

22. The absorbent article of claim 14, further including visual instructions disposed on the absorbent article, wherein an article pictured in the visual instructions has the same appearance as the actual absorbent article.

23. The absorbent article of claim 14, wherein a user facing side of the first and second belt portions of the waist belt and a user facing side of the first end portion of the absorbent section have a visual appearance different from the central portion of the absorbent section.

24. The absorbent article of claim 14, wherein the garment facing side of the waist belt and the user facing side of the waist belt are provided in the same color, pattern or texture.

25. The absorbent article of claim 14, wherein the garment facing side of the waist belt and the user facing side of the waist belt are provided in a different color, pattern, or texture.

26. The absorbent article of claim 14, wherein the fastening device for securing the second end portion of the absorbent section to the waist belt has the same appearance as the garment facing side of the first and second belt portions.

27. An absorbent article, comprising:
an absorbent section, the absorbent section having first and second end portions and a central portion therebetween;
a waist belt attached to the absorbent section, the waist belt having first and second belt portions extending on each side of the first end portion of the absorbent section such that the first and second belt portions can be secured directly to each other around a wearer of the absorbent article, at least one of the belt portions including a fastening device for securing the two belt portions directly to each other around a wearer of the absorbent article, the second end portion of the absorbent section including a fastening device for securing the second end portion of the absorbent section to the waist belt;
wherein a garment facing side of the first and second belt portions of the waist belt has a visual appearance different from the central portion of the absorbent section and garment facing sides of the first and second end portions of the absorbent section include a visual cue portion.

28. The absorbent article of claim 27, wherein the garment facing side of the first and second belt portions of the waist belt and the visual cue portion of the garment facing side of the first end portion of the absorbent section are colored, patterned or textured to give the appearance of a continuous belt.

29. The absorbent article of claim 27, wherein a first end of one of the first and second belt portions of the waist belt includes a grip portion.

30. The absorbent article of claim 29, wherein the grip portion is provided in a different color, pattern, texture or shape than a color, pattern, texture or shape of adjacent areas on the garment facing side of the first and second belt portions of the waist belt.

31. The absorbent article of claim 30, wherein the visual cue portion of the garment facing side of the second end portion of the absorbent section includes grip portions disposed on ends of the second end portion, the grip portions having a different color, pattern, texture or shape than adjacent areas on the garment facing side of the second end portion of the absorbent section.

32. The absorbent article of claim 27, wherein the visual cue portion of the garment facing side of the second end portion includes a colored, patterned, or textured section extending across the second end portion.

33. The absorbent article of claim 27, wherein the visual cue portion of the garment facing side of the second end portion of the absorbent section has the same color, pattern, or texture as the visual cue portion of the garment facing side of the first end portion of the absorbent section.

34. The absorbent article of claim 27, further including visual instructions disposed on the absorbent article, wherein an article pictured in the visual instructions has the same appearance as the actual absorbent article.

35. The absorbent article of claim 27, wherein a user facing side of the first and second belt portions of the waist belt and a user facing side of the first end portion of the absorbent section have a visual appearance different from the central portion of the absorbent section.

36. The absorbent article of claim 27, wherein the garment facing side of the waist belt and the user facing side of the waist belt are provided in the same color, pattern, or texture.

37. The absorbent article of claim 27, wherein the garment facing side of the waist belt and the user facing side of the waist belt are provided in a different color, pattern, or texture.

38. The absorbent article of claim 27, wherein the fastening device for securing the second end portion of the absorbent section to the waist belt has the same appearance as the garment facing side of the first and second belt portions.

* * * * *